(12) United States Patent
Rezai et al.

(10) Patent No.: US 8,538,536 B2
(45) Date of Patent: Sep. 17, 2013

(54) METHODS OF IMPROVING NEUROPSYCHOLOGICAL FUNCTION IN PATIENTS WITH NEUROCOGNITIVE DISORDERS

(75) Inventors: Ali Rezai, Shaker Heights, OH (US); Cynthia S. Kubu, Shaker Heights, OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 998 days.

(21) Appl. No.: 12/106,740

(22) Filed: Apr. 21, 2008

(65) Prior Publication Data

US 2008/0288018 A1 Nov. 20, 2008

Related U.S. Application Data

(60) Provisional application No. 60/907,887, filed on Apr. 20, 2007.

(51) Int. Cl.
*A61N 1/18* (2006.01)

(52) U.S. Cl.
USPC .............. 607/45; 607/116; 600/378; 600/545

(58) Field of Classification Search
USPC ................ 607/3, 45, 116, 139; 600/378, 545
See application file for complete search history.

(56) References Cited

U.S. PATENT DOCUMENTS

| | | | | |
|---|---|---|---|---|
| 6,094,598 A | * | 7/2000 | Elsberry et al. | 607/116 |
| 2002/0151939 A1 | * | 10/2002 | Rezai | 607/40 |
| 2005/0010262 A1 | * | 1/2005 | Rezai et al. | 607/46 |

OTHER PUBLICATIONS

Greenberg et al. "Three Year Outcomes in Deep Brain Stimulation for Highly Resistant Obsessive Compulsive Disorder." Neurospychopharmacology: 31, pp. 2384-2393. 2006.*

* cited by examiner

*Primary Examiner* — Carl H Layno
*Assistant Examiner* — Eugene Wu
(74) *Attorney, Agent, or Firm* — Tarolli, Sundheim, Covell & Tummino LLP

(57) ABSTRACT

The present invention provides methods of improving neuropsychological function in a patient having a neurocognitive disorder by chemical or electrically modulating a target site(s) in the ventral striatum/ventral capsule region. Methods also include modulating the treatment based on a closed-loop feedback system that measures bodily activities associated with the neuropsychological function (i.e. that help to determine whether a neuropsychological function is or can be improved.

11 Claims, 4 Drawing Sheets

METHODS OF IMPROVING NEUROPSYCHOLOGICAL FUNCTION IN PATIENTS WITH NEUROCOGNITIVE DISORDERS

CROSS-REFERENCE TO RELATED APPLICATIONS

The present application claims priority to U.S. Application No. 60/907,887, filed on Apr. 20, 2007, which is incorporated by reference herein.

BACKGROUND

Within the field of neuromodulation, the use of electrical modulation for treating neurological disease, such as Parkinson disease, essential tremor, dystonia, chronic pain, and epilepsy has been widely discussed in the literature. Neuromodulation includes administrating either or both of stimulating or inhibiting signals to increase, decrease or block neural activity. It has been recognized that electrical modulation holds significant advantages over lesioning. For example, lesioning results in irreversible destruction of neural tissue. Electrical modulation, on the other hand, permits modulation of the target neural structures and does not require the destruction of neural tissue.

Disorders manifesting gross physical dysfunction, not otherwise determinable as having psychiatric and/or behavioral origins, comprise the vast majority of those pathologies treated by deep brain stimulation. However, there have been disclosures on improving abnormal psychiatric function in psychiatric patients, such as those suffering from Obsessive Compulsive Disorder, depression and other psychiatric disorders. For example, efforts have been made to treat certain psychiatric disorders with peripheral/cranial nerve stimulation as well as deep brain stimulation. An investigational protocol in 2000 demonstrated partial benefits with vagus nerve stimulation in patients with depression (Biological Psychiatry 47: 216-286, 2000).

Methods of improving cognitive function have also been described by stimulating the intralaminar nuclei (see U.S. Pat. No. 6,539,263 to Nicholas Schiff).

However, these references either described treating psychiatric function in patients suffering from psychiatric diseases or describe improving cognitive function by stimulating very specific areas of the brain. A need exists to treat neuropsychological functions in patients suffering not from psychiatric disorders, but neurocognitive disorders. Further a need exists for modulating a region that affects neuropsychological function.

SUMMARY

The present invention is directed to improving neuropsychological function in a patient suffering from a neurocognitive disorder. Such a method is distinct from improving psychiatric function in a patient suffering from a psychiatric disorder or from improving neuropsychological behaivorper se (i.e. in a patient not suffering from a neurocognitive disorder). The method comprises positioning a delivery device, which can be an electrode or a drug port/catheter, in a target site of a ventral striatum/ventral capsule region of the brain and activating the delivery device to apply an activation signal to the target site to improve the neuropsychological function in the patient.

In certain embodiments, methods of improving neuropsychological function in a patient suffering from a neurocognitive disorder comprises positioning a delivery device in a ventral striatum/ventral capsule region of the brain and detecting a bodily activity of the brain associated with the neuropsychological function to produce a sensor signal. The method further comprises activating the delivery device to apply an activation signal to the target site based on the sensor signal to improve the neuropsychological function in the patient.

Other abbreviations are anterior commissure (ac); basolateral amygdaloid nucleus (BL); basomedial amygdaloid nucleus (BM); the claustrum (Cl); entorhinal cortex (Ent); fornix (f); hypothalamus (Hy); agranular insula (Ia); internal capsule (ic); lateral amygdaloid nucleus (La); optic tract (opt); optic chiasm (ox); subiculum (S); subcallosal area (SCA); thalamus (Th); and ventral claustrum (VCI).

Figure 1A:
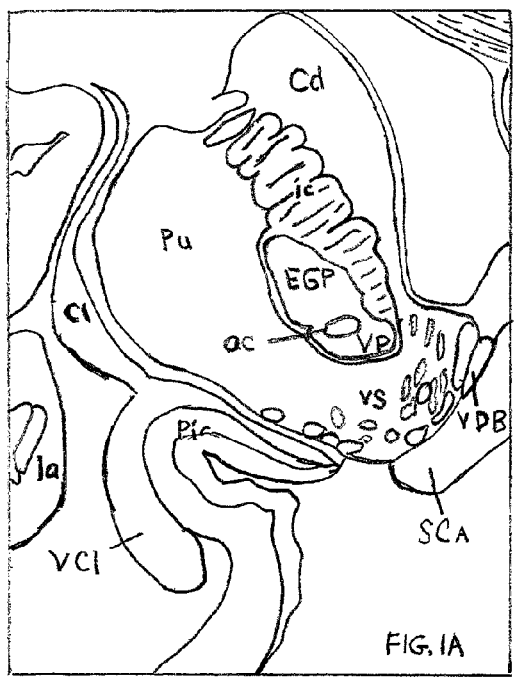
FIG. 1A-1D is a schematic illustrating of the human basal forebrain in a series of coronal sections from the level of accumbens (FIG. 1A) to the level of the caudal amygdala (FIG. 1D). The striatum includes the caudate nucleus (Cd); the putamen (Pu); and the ventral striatum (VS). The basal forebrain further includes the globus pallidus (external (EGP) and internal segments (IGP)); the ventral pallidum (VP); the basal nucleus of Meynert (B); the nucleus of the ventrical limb of the diagonal band (VDB) nucleus of the horizontal limb of the diagonal band (HDB); the piriform (olfactory) cortex (Pir); and the extended amygdala, which includes the lateral bed nucleus of stria terminalis (BSTL), the medial bed nucleus of stria terminalis (BSTM), the bed nucleus of stria terminalis, supra-capsular part/stria terminalis (BSTS/st), medial amygdaloid nucleus (Me), the sublenticular part of the extended amygdala (SLEA), and the central amygdaloid nucleus (Ce).
Figure 1B:
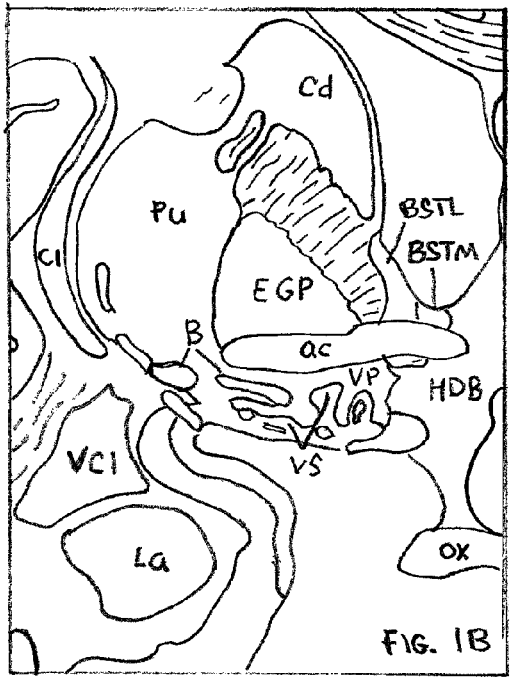
Figure 1C:
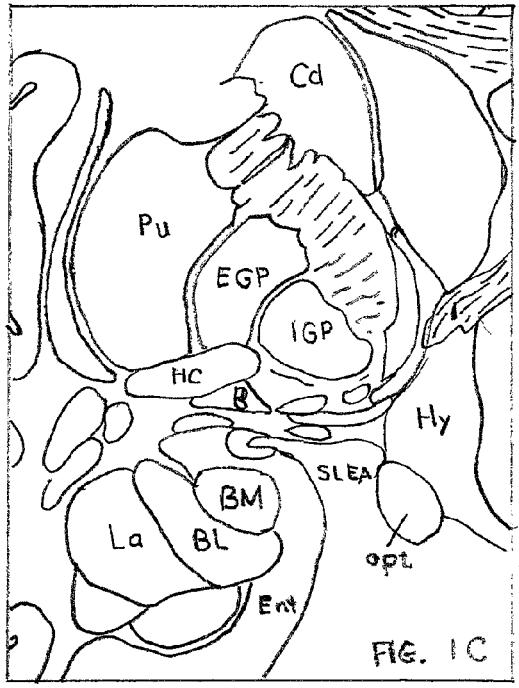
Figure 1D:
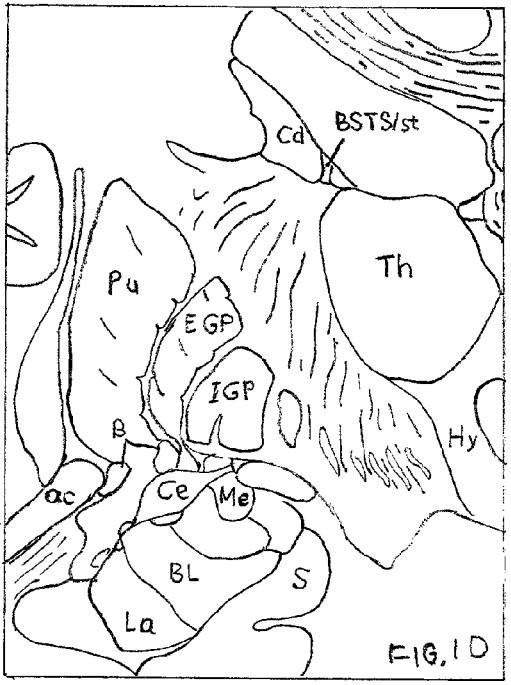
Figure 2:
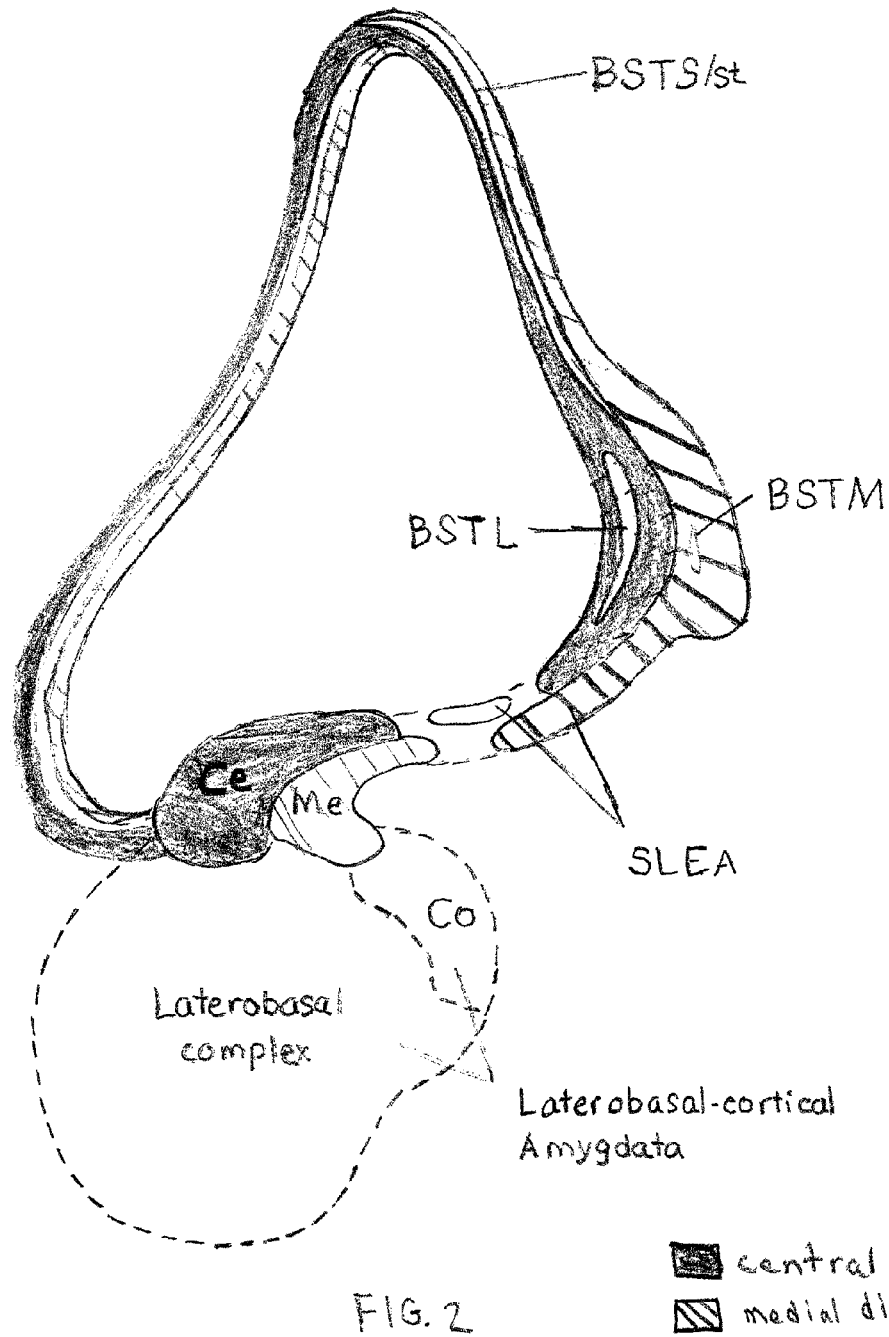

FIG. 2 is a schematic illustration of the extended amygdala shown in isolation from the rest of the brain, with the extensions of the central (Ce) and medial (Me) amygdaloid nuclei within the stria terminals (st) and through the sublenticular region to the bed nucleus of stria terminalis (BST). The central division of the extended amygdala is coded by filled in space and the medial division is coded by lined marks. Further abbreviations are the lateral bed nucleus of stria terminalis (BSTL); medial bed nucleus of stria terminalis (BSTM); supracapsular part of bed nucleus of stria terminalis/striaterminalis (BSTS/st); cortical amygdaloid nuclei (Co).

Figure 3:
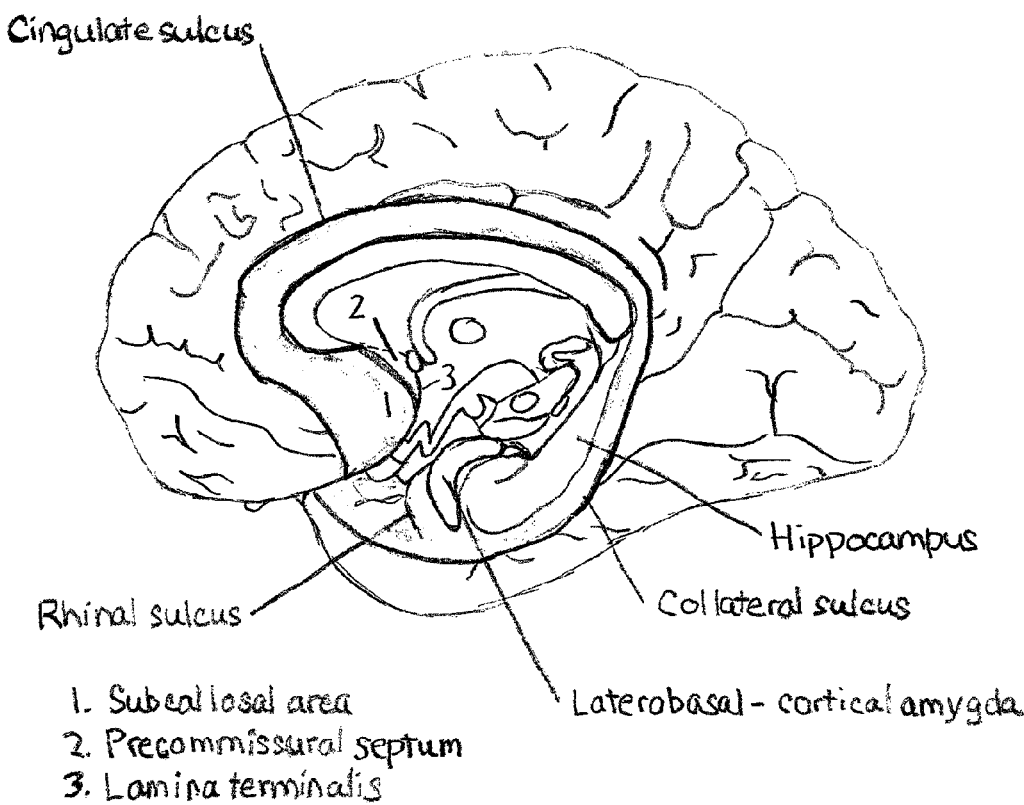

FIG. 3 is a schematic drawing of the medial surface of the hemisphere depicting the limbic lobe shaded. The laterobasal-cortical amygdala and hippocampus are projected on the surface of the parahippocampal gyrus.

Figure 4:
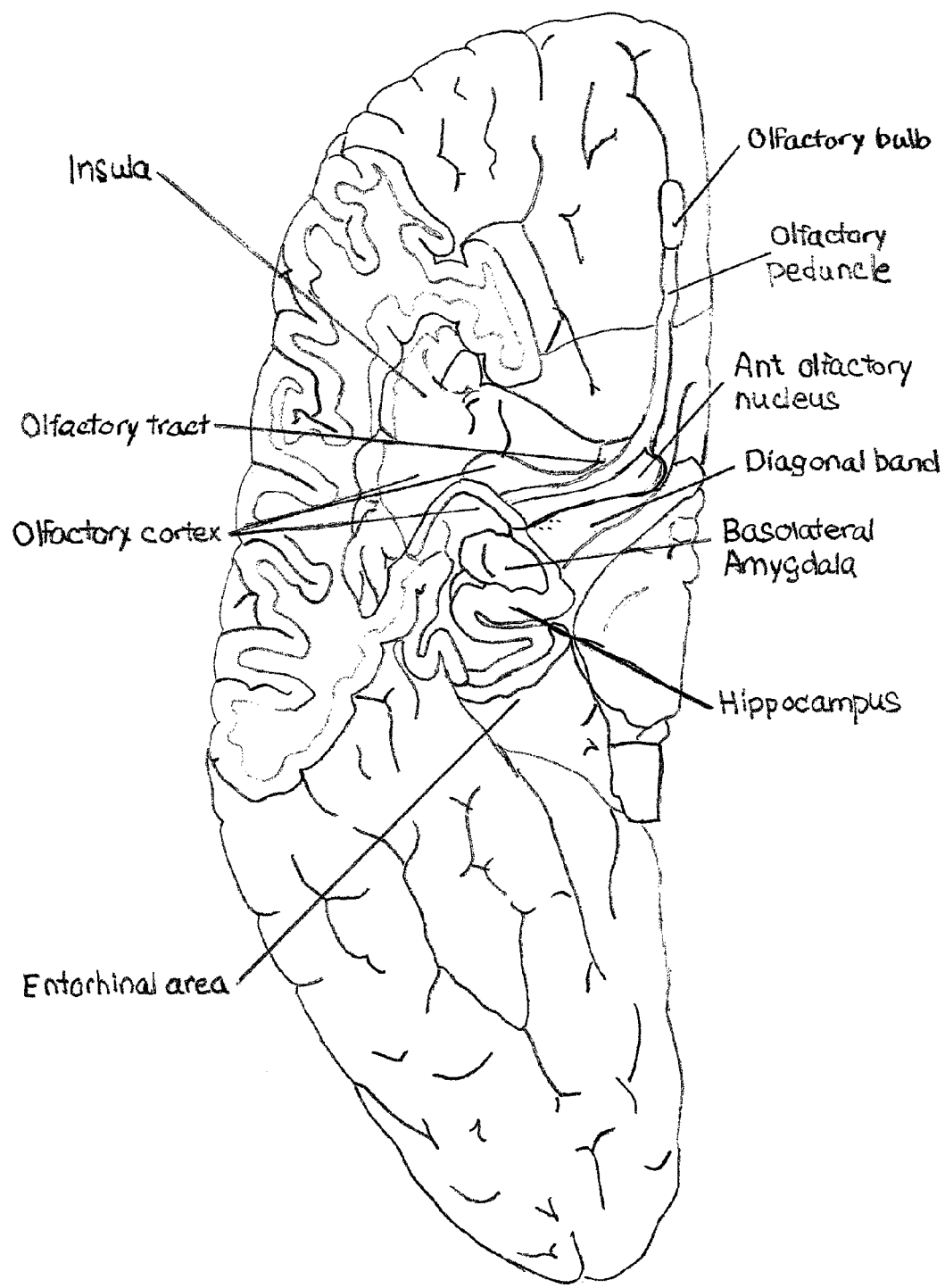

FIG. 4 is a schematic illustration of a basal view of human brain with the limbic lobe shaded. The filled in area is the primary olfactory cortex.

DETAILED DESCRIPTION

The present application provides methods of improving a neuropsychological function in a patient having a neurocognitive disorder. By "neuropsychological function" is meant behavioral expression of brain function, such as cognition, initiation, motivation, affect regulation, behavioral control, and perception and/or understanding of emotional stimuli characteristics. Non-limiting examples of neuropsychological functions are provided in Table I. Table I further provides common tests that can be used to assess certain neuropsychological functions. Of course, other battery of tests would be known to one of skill in the art for particular neuropsychological functions to be assessed.

TABLE I

| Neuropsychological Function | Exemplary Tests to Measure Neuropsychological Function |
| --- | --- |
| General intellectual function | Wechsler Abbreviated Scale of Intelligence and Wechsler Adult Intelligent Scale-III |
| Basic Attention | Digit Span, Spatial span subtests from the Wechsler Memory Scale-III |
| Complex Attention (working memory) | Digit Span, Letter Number Sequencing and Arithmetic subtests from the Wechsler Adult Intelligence Scale-III |
| Executive functions | Wisconsin Card Sorting Test; Trail Making Test B, Stroop Test, Tower of London Test; Gambling Test; Frontal System Behavior Scale; Iowa Scales of Frontal Lobe Function |
| Memory (visual and verbal) | Wechsler Memory Scales-III; Rey Auditory Verbal Learning Test; California Verbal Learning Test-II; Brief Visual Memory Test-Revised |
| Affect regulation | Minnesota Multiphasic Personality Inventory-2; Affective Stroop Test; Frontal System Behavior Scale; Iowa Scales of Frontal Lobe Function |
| Interpretation of Emotion Stimuli | DANVA |
| Processing Speed | Processing Speed index (Symbol Search, Coding) from the Wechsler Adult Intelligent Scale-III; Trail Making Test; and Symbol Digit Modalities Test |
| Language | Boston Naming Test; Controlled Oral Word Association Test; Semantic Word Fluency Test; and Multilingual Aphasia Examination |
| Visuo-constructional | Rey-Osterrieth Complex Figure Test; Block Design, and Object Assembly subtests from the Wechsler Adult Intelligence Scale-III |
| Visuo-spatial | Matrix Reasoning from the WAIS-III; Judgment of Line Orientation Test |

As can be seen from Table I, non-limiting examples of neuropsychological functions include general intellectual function; attention, such as basic attention, the ability to monitor and direct attention, and the flexible allocation of attentional resources; working memory or divided attention which refers to a limited-capacity memory system in which information that is the immediate focus of attention can be temporarily held and manipulated (such as, for example, being able to calculate the tip following a dinner at a restaurant or being able to simultaneously maintain two trains of thought in a flexible manner); executive functions which include, for example, planning, problem-solving skills, intentional and self-directed behavior, organizational skills, goal-directed behavior, the ability to generate multiple response alternatives, and maintenance of conceptual set (i.e. the ability to maintain (or not lose) set or track of what one is doing); the ability to evaluate and modify behavior in response to feedback; verbal and visual memory, or the ability to retain and store new information for future use; visuo-spatial skills, such as judging how lines are oriented or discerning spatial relationships and patterns; visuo-constructional skills including two-dimensional construction skills (such as, for example, drawing or completing puzzles) and three-dimensional constructional skills (such as, for example, arranging blocks to match a design); language such as confrontation naming (such as, for example, naming specific words on demand, such as when shown a picture of the object), word fluency or generating a nonredundant list of words that belong to a specific category; motivation/drive/initiation in the interpersonal, cognitive or behavioral domains; affect regulation (such the ability to control and direct affect and mood in an context appropriate manner); and interpretation of emotion stimuli (such as the ability to interpret emotional facial expressions, posture, body language, prosody, and contextual information in order to infer another's emotional state or help identify an appropriate emotional response). The present invention provides for improving any one or more of such neuropsychological functions. In a preferred embodiment, the neuropsychological function that is treated is memory (including visual and spatial) and/or learning.

Such neuropsychological functions can be measured by a variety of tests well known in the art. Exemplary tests are provided in Table I.

Although pure psychiatric function may be incidentally improved as well by methods of the present invention, the present invention is directed to improving neuropsychological function which is distinct from improvements in pure psychiatric function, such as improvements in obsessive-compulsive behavior (as measured, for example, by the Yale Brown Compulsive Scale (Y-BOCS); improvements in depression (as measured, for example, by the Hamilton Depression Rating Scale (HDRS) or the Montgomery Asberg Depression Rating Scale (MADRS); or improvements in Global Assessment of Function (GAF)).

Although psychiatric dysfunction can co-occur with neuropsychological dysfunction, neuropsychological function is distinct in that neuropsychological function is concerned with the underlying cognitive processes that are mapped to specific regions and circuits in the brain whereas psychiatric disorders refer to diagnoses indicated in the standard nomenclature such as the Diagnostic and Statistical Manual of Mental Disorders-IV and include disorders such as Anxiety Disorders, Mood Disorders, and Schizophrenia. In contrast, neuropsychological function refers to the underlying cognitive processes and their direct relationship to brain regions and circuits and can include, but is not limited to, the abilities listed above.

Furthermore, the present invention provides for improving neuropsychological function in a specific patient population—i.e. patients who suffer from a neurocognitive disorder, which is a disorder that primarily (and not secondarily) affects cognitive function. A patient with a neurocognitive disorders also manifests behavioral symptoms that reflect dysfunction involving the brain. Such symptoms include changes in cognition, drive, initiation, affect regulation, and social skills, that reflect underlying brain disorders or pathology either acquired, neurodevelopmental, or neurodegenerative. For example, a neurocognitive disorder can include dementias (such as, for example, Alzheimer disease, Fronto-temporal dementia), acquired brain injuries (such as, for example, traumatic brain injury, anoxic injuries), and neurodevelopmental disorders (such as, for example, autism).

A neurocognitive disorder according to the present invention does not include psychiatric disorders such as, for example, Obsessive Compulsive Disorder, a mood disorder such as depression including major depressive disorder or bipolar affective disorder; schizophrenia; or addiction.

Non-limiting examples of specific neurocognitive disorders are provided in Table II below.

TABLE II

| Neurocognitive Disorder Category | Examples of Specific Disorders within Category |
| --- | --- |
| Acquired Brain Injury Disorders | Traumatic brain injury, stroke (including ischemic, intracerebral hemorrhagic, subarchnoidal hemorrhagic), anoxic injuries, metabolic disorders, other systemic brain disorders (such as encephalitis), or brain injuries due to infection |

TABLE II-continued

| Neurocognitive Disorder Category | Examples of Specific Disorders within Category |
|---|---|
| Neurodevelopmental Disorders | Autism, dyslexia, attention deficit disorder |
| Neurodegenerative Disorders | Alzheimer disease and it's potential precursor Mild Cognitive Impairment, Frontotemporal dementia, Semantic dementia, Corticobasalganglionic degeneration, Lewy Body Disease, Parkinson disease and Parkinsonism |

Exemplary categories of neurocognitive disorders (and exemplary specific disorders within each category) and exemplary corresponding neuropsychological functions that can be improved according to the present invention is provided in Table III below.

TABLE III

| Neurocognitive Disorder | Exemplary Neuropsychological Function Improved |
|---|---|
| Dementia such as Alzheimer disease | Memory, apathy, attention, visuo-spatial skills, and/or language |
| Acquired Brain Injury such as subarachnoid aneurysm involving the anterior communicating artery | Memory, apathy, and/or goal directed intentional behavior |
| Neurodevelopmental disorder such as autism | Social communication, emotion recognition, and/or motivational behavior |

As shown in Tables II and III, non-limiting examples of acquired brain injury disorders include traumatic brain injury, stroke (including ischemic, intracerebral hemorrhagic, subarchnoidal hemorrhagic), anoxic injuries, metabolic disorders or other systemic brain disorders (such as, for example, encephalitis) that can affect neuropsychological functions including attention, working memory, processing speed, executive cognitive function, motivation/drive, language, visuo-spatial function, visuo-construction, and/or memory.

As shown in Tables II and III, non-limiting examples of neurodevelopmental disorders can include pervasive developmental disorders such as autism that are often associated with neuropsychological deficits that can affect attention, language, problem solving/executive function, affect regulation, interpretation of emotion stimuli, and/or drive/motivation.

In general, neurodegenerative disorders include, but are not limited to, dementia and the prodromal stages of dementia. Per current diagnostic criteria, dementia is defined as a deficit in memory and at least one other cognitive domain that represent a clear decline from premorbid levels of function and impacts day-to-day function. Examples of some neurodegenerative disorders include Alzheimer disease and it's potential precursor Mild Cognitive Impairment, Frontotemporal dementia, Semantic dementia, Corticobasalganglionic degeneration, Lewy Body Disease, Parkinson Disease Demention and other dementias that result in neuropsychological impairments that can affect memory, attention, processing speed, executive function, language, visuo-spatial skills, visuo-construction, memory, drive/motivation, interpretation of emotion stimuli, affect regulation, and/or learning.

The present invention provides methods of improving neuropsychological function in a patient having a neurocognitive disorder by positioning a delivery device in a target site of a ventral capsule/ventral striatum region of the brain and activating the delivery device to deliver an electrical and/or chemical signal to the target site. The ventral striatum/ventral capsule region as used herein refers to the ventral anterior limb of the internal capsule, the amygdala, the extended amygdala, the basal forebrain, the basal ganglia, and the ventral striatum (which includes nucleus accumbens). Stereotactic coordinates for this region are:

X—3 mm to 13 mm from the midline (medial lateral stereotactic region)

Y—5 mm behind AC to 10 mm in front of AC (Anterior-posterior stereotactic region)

Z—13 mm above the AC-PC line to 7 mm below the AC-PC line (dorsal/ventral stereotactic region).

Of course it is understood that more than one of the target sites in this region can be modulated simulataneously, concurrently or sequentially.

In certain embodiments, the basal ganglia is the ventral basal ganglia. In certain embodiments, the target site is the anterior limb of the internal capsule or the ventral striatum. In a preferred embodiment, the target site is the intersection between the ventral capsule and the ventral striatum.

In certain embodiments, the present invention provides for positioning a delivery device in the ventral capsule/ventral striatum circuitry, which are the regions of the brain that are in communication with (receive input from or provide output to) one or more of the above-referenced target sites of the ventral striatum/ventral capsule region of the brain. Such circuitry include the fibers connecting the frontal lobes, the limbic system, portions of the thalamus (excluding the intralaminar nuclei), regions of the ventral striatum (such as the nucleus accumbens and surrounding ventral striatum), the amygdala, extended amygdala, hippocampus, hypothalamus, ventral tegmental region, locus coeruleus, and substantia nigra, brain stem regions such as the ventral tegmental area, locus coeruleus. In a preferred embodiment, the target site is the ventral capsule, extended amygdala, basal forebrain or the ventral striatum. In a more preferred embodiment, the target site is the relatively compact region that represents a confluence of circuits involving the dorsolateral prefrontal lobe, anterior cingulate region, medial prefrontal cortex, orbitofrontal cortex, basal ganglia, thalamus (excluding the intralaminar nuclei), hypothalamus, basal forebrain, extended amygdala, amygdale, hippocampal circuit, hypothamalmus, ventral tegmental area, substantia nigra and locus coeruleus, junctional region or node of the ventral capsule and the ventral striatum through which various fibers interconnecting the medial, basal, and dorsolateral frontal lobes travel back and forth with interconnections to the thalamus (excluding the intralaminar nuclei) and the basal ganglia including the striatum and the pallidum. In any of the above embodiments, the target site is not the intralaminar nuclei. Table IV provides regions of this circuitry and specific, non-limiting target sites within this circuitry.

TABLE IV

| Region of Ventral Striatum/Ventral Capsule Circuitry | Specific Non-limiting Target Sites within Circuitry |
|---|---|
| Frontal Lobes | Cingulate cortex, orbitofrontal cortex, dorsolateral prefrontal cortex., medial prefrontal cortex |
| Memory Circuit | Hippocampus, parahippocampal gyrus, amygdala, fornix, mammillary bodies, basal forebrain, mammillothalamic tract, ventral anterior and mediodorsal nuclei of the thalamus, cingulum and cingulate gyrus, temporal lobe |

TABLE IV-continued

| Region of Ventral Striatum/Ventral Capsule Circuitry | Specific Non-limiting Target Sites within Circuitry |
|---|---|
| Limbic System | Cingulate gyrus, parahippocampal gyrus, olfactory cortex, caudal orbitofrontal cortex, medial prefrontal cortex, temporal pole cortex, anterior insula cortex, corticobasolateral complex of the amygdala, hippocampus, fornix, mammillary bodies |
| Basal ganglia/ventral striatum | Ventral caudate, ventral putamen, ventral pallidum, nucleus accumbens, olfactory tubercle, extended amygdala (including the centromedian nucleus of the amygdala and Bed Nucleus of the Stria Terminalus) |
| Basal Forebrain | Nucleus Basalis of Meynert, substantia innominata |
| Thalamus | Mediodorsal nucleus, ventral anterior nucleus, hypothalamus, mammillary bodies |

As can be seen from Table IV, the ventral capsule/ventral striatum circuitry constitutes the anterior limb of the internal capsule and fibers pathways connecting the frontal lobes, memory circuit, limbic system, basal ganglia (especially the ventral striatum), basal forebrain, and portions of the thalamus as well as regions of the basal forebrain, extended amygdala, ventral striatum (specifically the nucleus accumbens and surrounding ventral striatum). A region of this pathway are the frontal lobes, which include the cingulate cortex, particularly the anterior cingulate cortex; the orbitofrontal cortex, both the ventral and lateral components, and the dorsolateral prefrontal cortex. Another region of this pathway is the limbic system which includes the cingulate gyrus, the parahippocampal gyrus, the olfactory cortex, the caudal orbitofrontal cortex, medial prefrontal cortex, the temporal pole cortex, the anterior insula cortex, the corticobasolateral complex of the amygdala, the hippocampus and adjacent cortical regions, the fornix, and the mammillary bodies. Another region of this circuitry includes the basal ganglia/ventral striatum, which includes the ventral caudate, the ventral putamen, the ventral pallidum, nucleus accumbens, olfactory tubercle, and the extended amygdala. The human extended amygdala refers to the centromedial amygdala and its extensions into the subpallidal or sublenticular region near the stria terminalis with intimate links to the bed nucleus of the stria terminalus. The extended amygdala can best be envisioned as a ring that surrounds the internal capsule. Another region of this circuitry includes the basal forebrain including the nucleus basalis of Meynert. The basal nucleus of Meynert is part of a region often referred to as the substantia innominata. Another region of this circuitry includes the thalamus, which includes the mediodorsal nucleus, the ventral anterior nucleus, the hypothalamus and the mammillary bodies but excludes the intralaminar nuclei. Another region of this circuitry includes the hypothalamus, via connections to the basal forebrain and the limbic system. FIG. 1-4 provides schematic illustrations or flow charts of these target sites and in certain circumstances their interconnections to various other structures involved in the ventral capsule/ventral striatum circuitry.

Table V provides exemplary stereotactic coordinates for some of the target sites in the ventral capsule/ventral striatum circuitry as well as other brain sites that are part of this circuitry that can be targeted according to the present invention. It should be noted that these coordinates are merely exemplary to provide a general idea of the location of these structures. The exact coordinates may vary individual to individual but one skilled in the art could determine the location of such sites based on the below information.

TABLE V

| Target Structure | X | Y | Z |
|---|---|---|---|
| Periaqueductal gray | 2-4 mm lateral to midline | At PC up to 4 mm posterior | 2-4 mm below AC-PC |
| Basal Ganglia | | | |
| Ventral Striatum | 5-9 mm lateral to midline | −3 to +5 mm anterior to AC | 0-8 mm below the AC-PC |
| Ventral pallidum | 10-30 mm lateral to midline | −5 to +5 mm anterior to MCP | 10 mm above to 7 mm below AC-PC |
| Nucleus Accumbens | 3-10 mm lateral to midline | −3 to 10 mm anterior to AC | 0 to 7 mm below the AC-PC |
| Caudate nucleus | 12-25 lateral to midline | 0-10 mm anterior to AC | 0-15 mm above AC-PC |
| Anterior fornix | 1-3 mm lateral to midline | 0-3 mm posterior to AC | 0-5 mm superior to AC-PC |
| Posterior-medial hypothalamus | 1-4 lateral to midline | 3-5 mm posterior to AC | 3-5 inferior to AC-PC |
| Putamen | 20-30 mm lateral to midline | 10 mm posterior to 15 mm anterior to MCP | 5 mm inferior to 15 mm superior to AC-PC |
| Superior parietal lobule | On the lateral convexity of the hemispheres. Defined as the area posterior to the central sulcus, lateral to the midline and superior to the intraparietal sucus. | | |
| Meynert's nucleus (NBM) | 6-15 mm lateral to midline | 2 mm posterior to 3 mm anterior to AC | 5-9 mm inferior to AC-PC |
| Ventral anterior globus pallidus | 16-21 mm lateral to midline | 2-6 mm anterior to MCP | 1-6 mm inferior AC-PC |
| Ventral anterior subthalamic nucleus | 10-13 lateral to midline | 0-3 mm posterior to MCP | 2-6 mm inferior to AC-PC |
| Anterior limb of Internal capsule and peri-anterior commissural region | 7-15 mm lateral to midline | 3 mm posterior to 10 mm anterior to AC | 0-15 mm superior to AC-PC |
| Ventral tegmentum | 5-10 mm lateral to midline | 3-10 mm posterior to MCP | 2-5 mm inferior to AC-PC |

TABLE V-continued

| Target Structure | X | Y | Z |
|---|---|---|---|
| Pre-frontal cortex | Falx to sphenoid ridge | From 20 mm anterior to the coronal suture to the base of the skull | From the midline to the sylvian fissure |
| Orbital frontal cortex | From the gyrus rectus to the inferior frontal sulcus | From the anterior commissure to the frontal pole | Frontal fossa base to the cingulate sulcus |
| Cingulate cortex | 5-9 mm lateral to midline | 15-25 mm posterior to frontal horn tip | 1-5 mm above ventricular roof |
| Amygdala | 12-22 mm lateral to midline | 3-15 mm anterior to MCP | 15 to 25 mm inferior to AC-PC |
| Hippocampus | Lateral to the coronal fissure in the floor of the inferior horn | From the amygdala to 40 mm posterior | 10-20 mm inferior to AC-PC |
| Mammillary bodies | 0-5 mm lateral to midline | 2-12 mm anterior to MCP | 5 to 15 mm below AC-PC |
| Lateral hypothalamus | 5-15 mm lateral to midline | 7 mm anterior to 3 mm posterior to AC | 0-10 mm inferior below AC-PC |
| Brainstem | | | |
| Locus ceruleus | 0-7 mm lateral to midline | 10-20 mm posterior to MCP | 5 to 20 mm inferior to AC-PC |
| Dorsal Raphe Nucleus | 0-7 mm lateral to midline | 10-20 mm posterior to MCP | 3-15 mm inferior to AC-PC |
| Substancia Nigra pars compacta | 5-12 mm lateral to midline | 5 mm anterior to 10 mm posterior to MCP | 5 to 20 mm inferior to AC-PC |
| Substancia Nigra pars reticulata | 6-15 mm lateral to midline | 5 mm anterior to 10 mm posterior to MCP | 5 to 20 mm inferior to AC-PC |
| Anterior Nucleus of the thalamus | 2-12 mm lateral to midline | 0-10 mm anterior to MCP | 7-15 mm superior to AC-PC |
| Dorsomedial nucleus of the thalamus | 0-10 mm lateral to midline | 5 mm anterior to 5 mm posterior to MCP | 5-15 mm superior to AC-PC |
| Superior frontal gyrus | 0-26 mm lateral to midline | 75 mm anterior to 19 mm posterior to MCP | 36-67 mm superior to AC-PC |
| Middle frontal gyrus | 25-49 mm lateral to midline | 72 mm anterior to 17 mm posterior to MCP | 31-67 mm superior to AC-PC |
| Inferior frontal gyrus | 33-59 mm lateral to midline | 7.5-55 mm anterior to MCP | 5-31 mm superior to AC-PC |
| Medial frontal gyrus | 0-19.5 mm lateral to midline | 22-78 mm anterior to MCP | 10 mm inferior to 10 mm superior to AC-PC |
| Anterior cingulate | 7-10 mm lateral to midline | 35 mm ant to MCP or 2 mm ant to frontal horn | 25 mm above AC-PC or 7 mm above CC |
| Post-cingulate | 0-14 mm lateral to midline | 0 to 37 mm posterior to MCP | 22-36 mm above AC-PC |
| Parahippocampal gyrus | 16-29 mm lateral to midline | 7.67 anterior to 29 mm posterior to MCP | 6-27 mm below AC-PC |
| Anterior Medial Ventral Pallidum | 7-15 mm lateral to midline | 8 mm anterior to 2 mm posterior to MCP | 0-5 mm below AC-PC |

In certain embodiments, the present invention provides for identifying whether a patient should have the methods of the present invention performed. For example, in certain embodiments, neurophysiological tests are conducted prior to positioning the delivery device at the target site. Such tests can also be conducted during or after the procedure to determine suitable placement of the delivery device and suitable stimulation parameters that are effective in improving the neuropsychological function in the patient. Thus, such neurophysiological tests can be conducted prior to, during, and/or after placing the delivery device at the target site of the brain. Such neurophysiological tests include, but are not limited to, functional MRI, connectivity studies, diffusion tensor imaging, MEG, evoked potentials, and PET scans.

In embodiments where the delivery device is an electrode and the activation signal is an electrical signal, once the electrode is placed on a ventral striatum/ventral capsule target site or a target site of the ventral striatum/ventral capsule circuitry, a pulse generator connected to the electrode is activated thereby applying to the target site an electrical activation signal having specified pulsing parameters. The electrical signal may be applied continuously or intermittently and the pulsing parameters, such as the pulse width, amplitude, frequency, voltage, current, intensity, and/or waveform may be adjusted to achieve a desired result. Specifically, the degree in which the target site is stimulated to treat a neurocognitive disorder can be controlled by adjusting these parameters. Preferably, the electrical signal is operated at a voltage between about 1 to about 60 V. More preferably, the electrical signal is operated at a voltage between about 1 V to about 15 V. Even more preferably, the current is between about 2 to about 6 V. Preferably, the electric signal is operated at a frequency range between about 2 Hz to about 2500 Hz. More preferably, the electric signal is operated at a frequency range between about 2 Hz to about 200 Hz. Even more preferably, the frequency range is between about 130 to about 200 Hz. Preferably, the pulse width of the electrical signal is between about 10 microseconds to about 1,000 microseconds. More preferably, the pulse width of the electrical signal is between about 50 microseconds to about 500 microseconds. Even more preferably, the pulse width is between about 60 microseconds to about 200 microseconds.

The waveform may be, for example, biphasic square wave, triangular sine wave, or other electrically safe and feasible combination. Preferably, the application of the electrical signal is: monopolar when the electrode is monopolar, bipolar when the electrode is bipolar, and multipolar when the electrode is multipolar. Furthermore, the waveform can be a normal or modified signal as described in more detail in pending U.S. application Ser. No. 11/943,344 entitled: "Systems and Methods for Neuromodulation Using Pre-Recorded Waveforms" filed on Nov. 20, 2007, which is incorporated by reference herein.

The electrode may be placed in permanent or temporary communication with the target site to provide chronic or acute stimulation to the target site. Specifically, the electrical neuromodulation can be temporary or short term, such as less than 10 days, intermediate (10-30 days) or chronic (greater than 30 days). Further, the modulation can be directional in nature, applying an activation signal to only certain regions while sparing modulation to others. Specifically, the leads or catheters/drug ports (delivery device) used to deliver the activation signal can be directional in nature such that the electrodes or drug ports are capable of being selectively activated to deliver an electrical or chemical signal to only certain portions of the target region while sparing other regions. Such directional electrodes/drug ports allows for precise selective modulation of certain areas of the ventral striatum/ventral capsule region as well as allows steering of the activation signal. In addition to modulating the direction of the activation signal, the degree of activation that each electrode or drug port delivers can be adjusted. For example, the pulsing parameters of electrodes may be adjusted to initiate, stop, increase, or decrease the pole combinations, energy, amplitude, pulse width, waveform shape, frequency, and/or voltage or any other pulsing parameter known to one of skill in the art to adjust the degree of modulation delivered thereby. In a preferred embodiment, each electrode or drug port of the respective lead or catheter is selectively powerable such that the pulsing/chemical delivery parameters of the electrode or drug port can be adjusted independent of the pulsing parameters of another electrode or drug port.

In embodiments where the delivery device is a drug port or catheter and the activation signal is a chemical signal, the chemical signal can be delivered instead of or in addition to the electrical signal delivered by an electrode according to the above-described embodiment. Specifically, a chemical agent may be delivered to a target site prior to, concurrent with, subsequent to or instead of the electrical neuromodulation. The chemical agent may be a neurotransmitter mimic; neuropeptide; hormone; pro-hormone; antagonist, agonist, reuptake inhibitor, botox or other highly specific neurotoxins, or degrading enzyme thereof; peptide; protein; pharmaceutical agent; amino acid; nucleic acid; stem cell or any combination thereof and may be delivered by a slow release matrix or drug pump. Non-limiting examples of neurotransmitters include dopamine, serotonin, and GABA. The chemical agents may be delivered continuously or intermittently and the chemical neuromodulation can be temporary or short term, such as less than 10 days, intermediate (10-30 days) or chronic (greater than 30 days).

Notwithstanding whether chemical and/or electrical neuromodulation is employed in the methods of the present invention, a closed-loop feedback mechanism may be employed in conjunction with such neuromodulation. In such an embodiment, an activation signal is applied to a ventral striatum/ventral capsule region target site or a target site of the ventral striatum/ventral capsule circuitry in response to a detected bodily activity associated with the neuropsychological function. The bodily activity is associated with the neuropsychological function in that detection of the activity can determine whether the neuropsychological function is being improved or not by the neuromodulation. In particular, this embodiment includes placing a delivery device at a target site, detecting a bodily activity of the body associated with the neuropsychological function being improved to produce a sensor signal, and activating the therapy delivery device to apply an activation signal to the target site in response to the sensor signal. The method need not necessarily be performed in this order. For example, the bodily activity associated with the neuropsychological function desired to be improved can be measured prior to positioning the delivery device at the target site or prior to activating the delivery device. Such bodily activity to be detected is any characteristic or function of the body that can relate to neuropsychological function and thus can assist with making a determination as to whether the neuropsychological function is or can be improved. Non-limiting examples of suitable bodily activities include, for example, respiratory function, body temperature regulation, blood pressure, heart rate, flushing, temperature, GI response (and other autonomic response), metabolic activity, cerebral blood flow, pH levels, vital signs, galvanic skin responses, perspiration, electrocardiogram, electroencephalogram, action potential conduction, chemical production, body movement, response to external stimulation, speech, balance, motor activity, ocular activity, cognitive function, and any of the other neuropsychological functions described above.

In another embodiment of the present invention, the bodily activity of the body includes an electrical or chemical activity of the body that is associated with neuropsychological function and may be detected by sensors located on or within the body. For example, such activity may be detected by sensors located within or proximal to the target site, distal to the target site but within the nervous system, or by sensors located distal to the target site outside the nervous system. Examples of electrical activity detected by sensors located within or proximal to the target site include sensors that measure neuronal electrical activity, such as the electrical activity characteristic of the signaling stages of neurons (i.e. synaptic potentials, trigger actions, action potentials, and neurotransmitter release) at the target site and by afferent and efferent pathways and sources that project to and from or communicate with the target site. For example, the sensors can measure, at any signaling stage, neuronal activity of any of the diffuse connections of the ventral striatum/ventral capsule circuitry. In particular, the sensors may detect the rate and pattern of the neuronal electrical activity to determine the electrical signal to be provided to the electrode.

Examples of chemical activity detected by sensors located within or proximal to the target site include sensors that measure neuronal activity, such as the modulation of neurotransmitters, hormones, pro-hormones, neuropeptides, peptides, proteins, electrolytes, or small molecules by the target site and modulation of these substances by afferent and efferent pathways and sources that project to and from the target site. Specific neurotransmitters that can be measured include acetylcholine, which is relevant to the mesial temporal memory circuit. Other relevant neurotransmitters include dopamine, serotonin, norepinephrine, and GABA which are involved in modulating cognitive function. Other exemplary chemicals that can be measured are corticosteroids, particularly in the hippocampal region.

With respect to detecting electrical or chemical activity of the body by sensors located distal to the target site but still within the nervous system, such sensors could be placed outside the skull, in the brain, the spinal cord, cranial nerves, and/or spinal nerves or other peripheral nerves. Sensors placed in the brain are preferably placed in a layer-wise manner in the direction of increasing proximity to the target site. For example, a sensor could be placed on the scalp (i.e. electroencephalogram), in the subgaleal layer, on the skull, in the dura mater, in the sub dural layer and in the parenchyma (i.e. in the frontal lobe, occipital lobe, parietal lobe, temporal lobe) to achieve increasing specificity of electrical and chemical activity detection. The sensors could measure the same types of chemical and electrical activity as the sensors placed within or proximal to the target site as described above.

With respect to detecting electrical or chemical activity by sensors located distal to the target site outside the nervous system, such sensors may be placed in venous structures and various organs or tissues of other body systems, such as the endocrine system, muscular system, respiratory system, circulatory system, urinary system, integumentary system, and digestive system or such sensors may detect signals from these various body systems. All the above-mentioned sensing systems may be employed together or any combination of less than all sensors may be employed together.

In certain embodiments, the areas where sensors are placed are along any node of the ventral striatum/ventral capsule circuitry (as well as the motor circuitry). Such sites are described above but specifically include the frontal cortex, pre-frontal cortex, orbitofrontal cortex, caudate nucleus, putamen, globus pallidus, ventral pallidum, striatum, nucleus accumbens, pre-motor areas, supplementary motor areas, and ventral tegmental areas.

Also, as described above, various neurophysiological tests can be conducted to generate a sensor signal to which the delivery device responds.

After the sensor(s) detect the relevant bodily activity associated with the neuropsychological function desired to be improved, the sensors generate a sensor signal. The sensor signal is processed by a sensor signal processor and provides a control signal to the stimulation controller, which is a signal generator or drug pump depending on whether electrical or chemical neuromodulation is desired. The stimulation controller, in turn, generates a response to the control signal by, for example, activating the delivery device or aiding in determining the position of the delivery device, for example. The delivery device cab then apply or modulate application of an activation signal to the target site to improve the neuropsychological function. In the case of electrical neuromodulation, the control signal may be an indication to initiate, terminate, increase, decrease or change the rate or pattern of a pulsing parameter of the electrical stimulation and the activation signal can be the respective initiation, termination, increase, decrease or change in rate or pattern of the respective pulsing parameter. In the case of chemical neuromodulation, the control signal can be an indication to initiate, terminate, increase, decrease or change the rate or pattern of the amount or type of chemical agent administered, and the activation signal can be the respective initiation, termination, increase, decrease or change in the rate or pattern of the amount or type of chemical agent administered. The processing of closed-loop feedback systems for electrical and chemical stimulation are described in more detail in respective U.S. Pat. Nos. 6,058,331 and 5,711,316, both of which are incorporated by reference herein.

Although the application of sensors to detect bodily activity are within the scope and spirit of the present invention, the present invention also contemplates the relevant bodily activity to be detected without sensors. In such case the neuromodulation parameters are adjusted manually in response to the clinical course of the neurocognitive disorder or to reporting by the patient.

The foregoing description has been set forth merely to illustrate the invention and is not intended as being limiting. Each of the disclosed aspects and embodiments of the present invention may be considered individually or in combination with other aspects, embodiments, and variations of the invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. For example, although methods of treating specific neurocognitive disorders are described with respect to electrical and chemical neuromodulation, other modes of neuromodulation can be used such as light, magnetism, sound, pressure, and heat/cold. Furthermore, all references cited herein are incorporated by reference in their entirety.

We claim:

1. A method of improving neuropsychological dysfunction in a patient suffering from an acquired brain injury disorder or a neurodegenerative disorder, the method comprising:
   identifying a patient suffering from an acquired brain injury disorder or a neurodegenerative disorder;
   measuring the patient's neuropsychological function;
   determining if the patient suffers from neuropsychological dysfunction based on the measurement;
   placing a delivery device on a target site in the ventral striatum, ventral capsule, or intersection of the ventral capsule and ventral striatum of the patient;
   activating the delivery device to apply an activation signal to the target site; and
   identifying improvements in the neuropsychological dysfunction in the patient based on the activation.

2. The method of claim 1, further comprising:
   detecting a bodily activity associated with the neuropsychological function;
   determining if the neuropsychological function is being affected;
   producing a sensor signal based on the determination;
   modulating the activation signal based on the sensor signal; and
   identifying improvements in the neuropsychological function based on the modulation.

3. The method of claim 2, wherein detecting the bodily activity comprises conducting a neurophysiological test on the patient selected from the group consisting of: performing a functional MRI, performing connectivity studies, performing diffusion tensor imaging, performing magnetoencephalography, measuring evoked potentials, and performing a PET scan.

4. The method of claim 2, further comprising:
positioning the delivery device on the target site based on the sensor signal.

5. The method of claim 1, wherein the neuropsychological function is memory.

6. The method of claim 5, wherein the memory is verbal and/or visual memory.

7. The method of claim 1, wherein the neuropsychological function is visuo-spatial skills 8. The method of claim 1, wherein the neuropsychological function is attention, working memory, learning, thinking speed, problem solving/executive cognitive function, language, visuo-constructional skills, visuo-spatial skills, motivation, drive, affect regulation, or interpretation of emotion stimuli.

9. The method of claim 1, wherein the delivery device is an electrode and the activation signal is an electrical signal.

10. The method of claim 1, wherein the delivery device is a catheter or drug port and the activation is a chemical signal.

11. A method of improving neuropsychological dysfunction in a patient suffering from an acquired brain injury disorder or a neurodegenerative disorder, the method comprising:
identifying a patient suffering from an acquired brain injury disorder or a neurodegenerative disorder;
measuring the patient's neuropsychological function;
determining if the patient suffers from neuropsychological dysfunction based on the measurement;
activating a delivery device to apply an activation signal to a target site of the ventral striatum, ventral capsule, or intersection of the ventral capsule and ventral striatum of the patient in response to a sensor signal which detects a bodily activity associated with the neuropsychological function; and
identifying improvements in the neuropsychological dysfunction in the patient based on the sensor signal.

* * * * *